United States Patent [19]

Flom

[11] Patent Number: 4,595,586

[45] Date of Patent: Jun. 17, 1986

[54] MOISTURIZING LOTION

[75] Inventor: Merlyn G. Flom, Noblesville, Ind.

[73] Assignee: Eli Lilly and Company, Indianapolis, Ind.

[21] Appl. No.: 771,450

[22] Filed: Aug. 30, 1985

[51] Int. Cl.$^4$ .......................... A61K 7/42; A61K 7/44
[52] U.S. Cl. ......................................... 424/59; 424/47; 424/60; 514/783; 514/846; 514/847; 514/873
[58] Field of Search ..................... 514/847; 424/59, 60

[56] References Cited

U.S. PATENT DOCUMENTS

| | | | |
|---|---|---|---|
| 4,268,502 | 5/1981 | Martin | 514/390 |
| 4,268,526 | 5/1981 | Vargas et al. | 514/770 |
| 4,272,519 | 6/1981 | Herrold et al. | 424/83 |
| 4,272,544 | 6/1981 | Cella et al. | 514/171 |
| 4,368,187 | 1/1983 | Flom et al. | 514/847 |
| 4,368,189 | 1/1983 | Mentlik | 514/847 |
| 4,372,944 | 2/1983 | Herrold | 514/847 |

OTHER PUBLICATIONS

Clinique Ingredient Label, 6/19/79.
Visible Difference Ingredient Label, 4/30/74.

*Primary Examiner*—Dale R. Ore
*Attorney, Agent, or Firm*—Bruce J. Barclay; Arthur R. Whale

[57] ABSTRACT

The present invention provides a novel moisturizing lotion which increases the rate of cell renewal on the skin without causing skin irritation and which facilitates the subsequent application of make-up.

3 Claims, No Drawings

MOISTURIZING LOTION

BACKGROUND OF THE INVENTION

A number of products are commercially available which are directed to moisturizing the skin, thereby helping to maintain its youthful appearance and soft texture. While these products achieve varying degrees of success as moisturizing agents, research continues in an effort to develop more effective moisturizing agents.

Cells of the skin are constantly being generated during the natural cell renewal cycle of the skin. This cell renewal cycle involves the generation of new cells which rise through the epidermal layers of the skin until they reach the outer epidermal layer, or stratum corneum, where the skin cells die and eventually fall, or slough, off. Young skin renews its surface layers every two to three weeks, whereas mature skin may take twice as long to be renewed as compared to young skin. The longer the cell renewal process takes, the greater the loss of natural moisture on the skin's surface thereby making the skin feel dry.

By accelerating the renewal of cells on the skin, the skin can be made to appear younger and fresher looking. Many moisturizers currently available cause such acceleration by irritating the skin's surface to such a degree so as to cause sloughing off of stratum corneum cells. However, such irritation is not desired because of the potential damage to the skin.

The present invention provides a new moisturizer in lotion form having many of the properties of an ideal moisturizer. For example, the lotion provides excellent moisturization and increases the cell turnover rate on the stratum corneum without irritation. The lotion has been found to be non-comedogenic. The lotion is an excellent base for make-up, and not only can be worn under make-up, but actually facilitates the smooth application of make-up. Further, since overexposure of the skin to the sun may lead to premature aging of the skin, the composition of the invention contains a sunscreen to help minimize this effect.

SUMMARY OF THE INVENTION

The present invention relates to a novel moisturizing lotion which increases the rate of cell turnover in the skin without irritation and facilitates the subsequent application of make-up.

DETAILED DESCRIPTION OF THE INVENTION

The terminology employed herein to describe the generic ingredients of the present moisturizing lotion are all names adopted by The Cosmetic, Toiletry and Fragrance Association, Inc., and are listed in their cosmetic ingredient dictionary.

The moisturizing lotion of the present invention, in addition to increasing the cell renewal rate of the skin without irritation, provides an excellent base over which make-up and other cosmetics may be applied. The formulation is nonirritating due to the use of a nonionic emulsification system which is comprised of nonionic emulsifiers and partially neutralized fatty acids. It is unique that such an emulsification system can be incorporated with other formulation ingredients to provide a stable lotion system with unique properties. The present composition is an excellent moisturizer in lotion form. Creams are cosmetics known for their excellent moisturizing properties, but typically these properties are not seen with a lotion.

The moisturizing lotion of the present invention consists essentially of the following ingredients, in percent by weight, of a quality and purity suitable for cosmetic use:

| Ingredient | Weight Percent |
| --- | --- |
| carbomer 941 | 0.1 |
| glycerin | 4.5 |
| xanthan gum | 0.1 |
| allantoin | 0.2 |
| panthenol | 1.0 |
| triethanolamine | 0.3 |
| stearic acid | 0.5 |
| PEG-100 stearate | 1.0 |
| glyceryl stearate | 1.0 |
| cetyl alcohol | 1.0 |
| isostearic acid | 2.5 |
| squalane | 2.8 |
| cetearyl octanoate | 1.5 |
| mineral oil and lanolin alcohol (85:15, w:w) | 2.0 |
| jojoba oil | 2.5 |
| corn oil | 0–0.4 |
| dioctyl adipate, octyl stearate and octyl palmitate (25:41:34, w:w:w) | 3.0 |
| corn oil, BHA and BHT (3:1:1, w:w:w) | 0.05 |
| sunscreen(s) | 1.4–3.0 |
| preservatives | 0.1–1.0 |
| colorant(s) | 0.001–0.005 |
| fragrance | 0.05–0.5 |
| deionized water | q.s. to 100% |

Each of the specific ingredients listed above are known and commercially available. A brief discussion of preservatives, sunscreens, colorants and fragrances will follow.

All cosmetic compositions must be protected against the growth of potentially harmful microorganisms, and therefore preservatives are added as a routine. Generally from one tenth of one percent by weight to one percent by weight of preservatives are adequate, with 0.8 weight percent preferred by the present compositions. The traditional preservatives for cosmetics and pharmaceuticals are alkyl esters of para-hydroxybenzoic acid. Other preservatives which are commonly used include hydantoin derivatives, propionate salts, quaternium-15, imidazolidinyl urea, EDTA and its salts, and the like. Cosmetic chemists are familiar with appropriate preservatives and routinely choose them to satisfy preservative challenge testing and to provide product stability. Particularly preferred preservatives for the preferred emulsion product of this invention are methyl and propyl para-hydroxybenzoates and 2-phenoxyethanol. The preservatives should be selected having regard for the use of the composition and possible incompatibilities between the preservatives and the other ingredients in the lotion.

It is known that overexposing skin to the sun leads to premature aging of skin. As such, the present moisturizing lotion contains from about 1.4 percent to about 3.0 percent by weight of a sunscreen in an effort to minimize this effect of the sun. This sunscreen may be any of the p-aminobenzoic acid derivatives having the ability to block out the sun's harmful rays, including octyl dimethyl PABA, which is preferred. Other sunscreens include octyl methoxycinnamate, benzophenon-3, -4 and -8 and butyl methoxydibenzoylmethane. Sunscreens may be used either alone or in combination to obtain the desired protection from harmful rays.

The compositions of the invention will also contain one or more colorants to provide an aesthetically pleasing color to the lotion, and typically one, but possibly more, fragrances which are non-irritating to the skin and soothing to the olfactory system. These ingredients are employed at concentrations as hereinbefore described.

While the compositions of the invention are preferably employed as a lotion, the composition may also be used in other forms as well. One such other form would be a mousse formulation containing from about 2.0% to about 15.0% by weight of a standard propellant.

The following Examples further illustrate the compositions of the invention, and methods for their manufacture. The Examples are illustrative only, and are not intended to be limiting to the scope of the invention in any respect.

EXAMPLE 1

A moisturizing lotion of the present invention having a sunscreen providing a protection factor of 4 was prepared with the following ingredients by weight percent:

| Phase | Ingredients | Weight Percent |
|---|---|---|
| A | deionized water | 10.0 |
|   | Carbopol 941 (carbomer 941, a polymer of acrylic acid crosslinked with a polyfunctional agent, from B. F. Goodrich Chemical Co., Cleveland, Ohio) | 0.1 |
| B | glycerin | 4.5 |
|   | xanthan gum | 0.1 |
| C | deionized water | 62.45 |
| D | methylparaben | 0.25 |
|   | allantoin | 0.2 |
|   | panthenol | 1.0 |
|   | triethanolamine (98%) | 0.3 |
| E | stearic acid | 0.5 |
|   | PEG-100 stearate and glyceryl stearate (1:1, w:w) | 2.0 |
|   | cetyl alcohol | 1.0 |
|   | isostearic acid | 2.5 |
|   | Robane (squalane from Robeco Chemicals, Inc., New York, New York) | 2.8 |
|   | Pur-Cellin Oil (cetearyl octanoate from Dragoco, Inc., Totowa, New Jersey) | 1.5 |
|   | Amerchol L-101 (a mixture of mineral oil and lanolin alcohol, 85:15, w:w, from Amerchol Corp., Edison, New Jersey) | 2.0 |
|   | jojoba oil | 2.5 |
|   | corn oil | 0.4 |
|   | Escalol 507 (octyl dimethyl p-aminobenzoic acid sunscreen from Van Dyk and Company, Inc., Belleville, New Jersey) | 2.0 |
|   | Wickenol 103 (a mixture of dioctyl adipate, octyl stearate and octyl palmitate, 25:41:34, w:w:w, from Wickhen Products, Inc., Huguenot, New York) | 3.0 |
|   | Tenox 4 (a mixture of corn oil, BHA and BHT, 3:1:1, w:w:w, from Tennessee Eastman Co., Kingsport, Tennessee) | 0.05 |
|   | propylparaben | 0.15 |
| F | 2-phenoxyethanol | 0.4 |
| G | deionized water | 0.04875 |
|   | FD & C Red #4 | 0.00055 |
|   | FD & C Yellow #5 | 0.00070 |
| H | fragrance | 0.25 |

The formulation was prepared as follows. Phase A was prepared one day prior to manufacture of the composition by adding the Carbopol 941 to the deionized water under vigorous agitation until the Carbopol was completely hydrated. Phase A was agitated just prior to use on the following day. Phase B was prepared by sprinkling the xanthum gum in the glycerin, and mixing with a propeller stirrer until uniformly dispersed. Phase B was agitated continuously until just prior to its use. Phase B was added to Phase C and mixed with a homogenizer and sweep stirrer until all of the xantham gum was hydrated. Phase D was dissolved into Phase BC while heating to about 85° C. Phase E was heated in a separate container to about 85° C. and added to Phase BCD. The resulting mixture was mixed at about 85° C. until homogeneous. Phase BCDE was cooled while homogenizing and sweep stirring. When the temperature of the mixture was about 55° C., homogenizing was discontinued and phase A was added to phase BCDE and mixed with the sweep stirrer until the mixture was homogeneous. The mixture was cooled with agitation, and when the temperature of phase ABCDE reached about 35° C., phase F, phase G and phase H were added. The mixture was mixed until uniform and cooling was continued to about 25° C.

EXAMPLE 2

A formulation of the invention was prepared by an alternate procedure having the following ingredients:

| Phase | Ingredients | Weight Percent |
|---|---|---|
| A | stearic acid | 0.5 |
|   | isostearic acid | 2.5 |
|   | Robane | 2.8 |
|   | Pur-Cellin Oil | 1.5 |
|   | PEG-100 stearate | 1.0 |
|   | glyceryl stearate | 1.0 |
|   | Amerchol L-101 | 2.0 |
|   | propylparaben | 0.15 |
|   | cetyl alcohol | 1.0 |
|   | jojoba oil | 2.5 |
|   | Tenox 4 | 0.05 |
|   | octyl dimethyl p-aminobenzoic acid | 2.0 |
|   | corn oil | 0.4 |
|   | Wickenol 163 | 3.0 |
| B | deionized water | 10.0 |
|   | Carbopol 941 | 0.1 |
| C | deionized water | 62.49875 |
|   | glycerin | 4.5 |
|   | methylparaben | 0.25 |
|   | triethanolamine (98%) | 0.3 |
|   | allantoin | 0.2 |
|   | panthenol | 1.0 |
|   | xanthum gum | 0.1 |
| D | 2-phenoxyethanol | 0.4 |
| E | FD & C Red #4 | 0.00055 |
|   | FD & C Yellow #5 | 0.0007 |
| F | fragrance | 0.25 |

The formulation of Example 2 was prepared as follows. The ingredients of phase A were combined and heated to about 80° C. while mixing with a Lightnin' mixer. In a separate vessel the components of phase C were combined and heated to about 80° C. while mixing with a Lightnin' mixer. Phase A was added to phase C and the mixture was allowed to cool while under agitation. When phase AC was at a temperature of about 60° C., phase B was slowly added while homomixing with very low shear for about 5 minutes. The mixture was then blended with a Lightnin' mixer until the temperature was about 40° C. Next, phases D, E and F were added in sequence to phase ABC. The composition was mixed and cooled to room temperature. The weight of the composition was 1000 g.

EXAMPLE 3

The following formulation was prepared as described in Example 2.

| Phase | Ingredients | Weight Percent |
|---|---|---|
| A | stearic acid | 0.5 |
|   | isostearic acid | 2.5 |
|   | Robane | 2.8 |
|   | Pur-Cellin Oil | 1.5 |
|   | PEG-100 stearate | 1.0 |
|   | glyceryl stearate | 1.0 |
|   | Amerchol L-101 | 2.0 |
|   | propylparaben | 0.15 |
|   | cetyl alcohol | 1.0 |
|   | jojoba oil | 2.5 |
|   | Tenox 4 | 0.05 |
|   | octyl dimethyl p-amino benzoic acid | 2.0 |
|   | butyl methoxydibenzoylmethane | 1.00 |
|   | Wickenol 163 | 3.0 |
| B | deionized water | 10.0 |
|   | Carbopol 941 | 0.1 |
| C | deionized water | 61.89875 |
|   | glycerin | 4.5 |
|   | methylparaben | 0.25 |
|   | triethanolamine (98%) | 0.3 |
|   | allantoin | 0.2 |
|   | panthenol | 1.0 |
|   | xanthum gum | 0.1 |
| D | 2-phenoxyethanol | 0.4 |
| E | FD & C Red #4 | 0.00060 |
|   | FD & C Yellow #5 | 0.00065 |
| F | fragrance | 0.25 |

The present invention also provides a method of moisturizing dry skin comprising treating susceptible dry skin with an effective amount of a moisturizing lotion of the invention. Such an amount will be sufficient to cover the surface of the skin with a thin coat of the lotion, which is frequently rubbed or massaged into the skin until the composition appears to have completely absorbed. When the present composition is used in accordance with the method of this invention, the rate of skin cell turnover is increased without skin irritation.

The following procedure was used to determine irritation of human skin following topical application of a number of cosmetic formulations. This procedure, termed the Lanman-Maibach test, was first described by B. M. Lanman at the Joint Conference on Cosmetic Sciences, Apr. 21-23, 1968 in Washington, D.C., and subsequently modified by Phillips et al. in *Toxicology and Applied Pharmacology* 21, 369-382 (1972). The subjects were evaluated daily for 21 days following application of the specified composition. The composition was applied to the same site daily, and prior to the next daily application, irritation was evaluated on a 0-3 scale. The irritancy was classified according to the following scale:

| 0-49 | Mild material - no experimental irritation |
| 50-199 | Probably mild in normal use |
| 200-449 | Possibly mild in normal use |
| 450-580 | Experimental cumulative irritation |
| 581-630 | Experimental primary irritant |

Example 1 of the present invention gave a value of 0 in this test, whereas Nutribel from Lancome, division of Cosmair, Inc., New York, N.Y. gave a score of 78 and Clinique Dramatically Different Moisturing Lotion from Clinique gave a score of 313.

The following experiment was conducted in order to demonstrate the ability of a formulation of the invention to accelerate the renewal of cells on the skin. In the experiment, dansyl chloride serves as the marker and its disappearance from the stratum corneum illustrates the transit time of cell renewal through the stratum corneum. Fourteen caucasian women ranging in age from twenty-five to forty years were used as subjects. Four areas were marked on the upper arms of each of the subjects on two sites per arm. Approximately 0.05 g of 5% dansyl chloride in white petrolatum was applied to one site on each arm 24 hours prior to application of the formulation. The formulation of Example 3 was applied randomly to one of the two test sites at a rate of 3 microliters/centimeter squared on the respective site, and was applied once daily Monday through Friday to the designated site until cell turnover was complete. The test sites were examined daily Monday through Friday using a uv light source to determine the presence of dansyl chloride fluorescence. The results of the tests appear below in Table I.

TABLE I

Stratum Corneum Transit Times
No. Days for Dansyl Chloride Dissappearance

| Subject | Treated | Untreated | Difference |
|---|---|---|---|
| 1 | 18 | 19 | 1 |
| 2 | 15 | 22 | 7 |
| 3 | 20 | 27 | 7 |
| 4 | 22 | 34 | 12 |
| 5 | 11 | 21 | 10 |
| 6 | 18 | 28 | 10 |
| 7 | 22 | 29 | 7 |
| 8 | 15 | 21 | 6 |
| 9 | 21 | 27 | 6 |
| 10 | 15 | 27 | 12 |
| 11 | 19 | 22 | 3 |
| 12 | 19 | 25 | 6 |
| 13 | 15 | 21 | 6 |
| 14 | 15 | 21 | 6 |
| Mean | 17.5 | 24.57 | 7.07 |
|  | SD = 3.10 | $P < 0.01$ |  |

As the data in Table I indicates, compositions of the invention accelerate the renewal of cells on the skin.

A study was also conducted in order to evaluate the moisturization efficacy of a composition of the invention. Twenty females ranging in age from eighteen to forty-five years having dry skin were used as subjects. Subjects were not permitted to use moisturizers or lotions on their legs for two-weeks prior to the initiation of the study. Objective evaluations were made at 7, 5 and 3 days prior to the application of the lotion. Subjects having moderately dry skin or severely dry skin with flaking and peeling were accepted into the study. Subjects were treated with a composition twice daily for a period of three weeks with one treatment in the morning and one treatment in the evening. After two to three days significant improvement occurred and remained during the 21 day period. After 21 days the average value of the twenty subjects was approximately 0.3 according to the following scoring scale.

0=smooth, no evidence in dryness
1=slightly dry skin
2=mildly dry skin
3=severely dry skin, flaking, peeling For 14 days following the cessation of application of the invention composition, the moisturization affect remained for 14 days with the average score of approximately 2.

The moisturization study was also conducted to illustrate the improved texture of the skin when using a composition of the invention. Impressions were taken of the legs with a silicone based polymeric material prior to treatment and at 14 and 21 days after treatment. Impressions were reviewed by three trained evaluators with a microscope at five times magnification. All evaluators were instructed to select the impression with better texture, and a correct response is where the treated skin had a better texture than untreated skin. The results of this test are presented below in Table II.

TABLE II

Skin Texture Study
No. of Correct Responses
(Days After Initiation of Study)

| Evaluator | 14 | 21 | P |
|---|---|---|---|
| 1 | 20/20 | 17/19* | <0.001 |
| 2 | 19/19* | 18/20 | <0.001 |
| 3 | 19/19* | 18/19* | <0.001 |

*one no difference

Formulations of the invention were also treated using standard human and animal models and found to be non-comedogenic.

Several formulations without a sunscreen, but otherwise identical to the present formulations, were also tested in the tests described above and found to give comparable results to those provided for formulations of the invention. From this it is concluded that the sunscreen does not contribute appreciably to the excellent and unique properties of the present formulations.

I claim:

1. A moisturizing lotion which facilitates make-up application and increases cell-turnover rate consists essentially of the following ingredients, in percent by weight:

| Ingredient | Weight Percent |
|---|---|
| carbomer 941 | 0.1 |
| glycerin | 4.5 |
| xanthan gum | 0.1 |
| allantoin | 0.2 |
| panthenol | 1.0 |
| triethanolamine | 0.3 |
| stearic acid | 0.5 |
| PEG-100 stearate | 1.0 |
| glyceryl stearate | 1.0 |
| cetyl alcohol | 1.0 |
| isostearic acid | 2.5 |
| squalane | 2.8 |
| cetearyl octanoate | 1.5 |
| mineral oil and lanolin alcohol (85:15, w:w) | 2.0 |
| jojoba oil | 2.5 |
| corn oil | 0–0.4 |
| dioctyl adipate, octyl stearate and octyl palmitate (25:41:34, w:w:w) | 3.0 |
| corn oil, BHA and BHT (3:1:1, w:w:w) | 0.05 |
| sunscreen(s) | 1.4–3.0 |
| preservatives | 0.1–1.0 |
| colorant(s) | 0.001–0.005 |
| fragrance | 0.05–0.5 |
| deionized water | q.s. to 100% |

2. The lotion of claim 1 which contains 0.25 weight percent methylparaben, 0.15 weight percent propylparaben and 0.40 weight percent 2-phenoxyethanol as preservatives.

3. A method of moisturizing dry skin comprising treating susceptible dry skin with an effective amount of a moisturizing lotion of claim 1.

* * * * *